United States Patent [19]

Hodgkins

[11] Patent Number: 4,805,611

[45] Date of Patent: Feb. 21, 1989

[54] ASPIRATING DEVICE

[75] Inventor: Harold M. Hodgkins, East Brunswick, N.J.

[73] Assignee: Becton, Dickinson and Company, Franklin Lakes, N.J.

[21] Appl. No.: 154,665

[22] Filed: Feb. 10, 1988

[51] Int. Cl.[4] ............................................ A61M 16/00
[52] U.S. Cl. ................................ 128/207.14; 604/171
[58] Field of Search .................. 604/171, 172, 173, 35, 604/118, 119, 163, 902; 128/207.14, 207.15, 207.16

[56] References Cited

U.S. PATENT DOCUMENTS

| | | |
|---|---|---|
| 3,319,628 | 5/1967 | Halligan . |
| 3,902,500 | 9/1975 | Dryden . |
| 3,991,762 | 11/1976 | Radford . |
| 4,300,550 | 11/1981 | Gandi et al. . |
| 4,569,344 | 2/1986 | Palmer . |
| 4,638,539 | 1/1987 | Palmer . |
| 4,691,702 | 9/1987 | Chantzis . |

Primary Examiner—Stephen C. Pellegrino
Attorney, Agent, or Firm—John L. Voellmicke

[57] ABSTRACT

An aspirating device includes a flexible catheter having a proximal first end, a distal second portion including a second end and a passageway therethrough. The catheter is adapted for insertion into the trachea of a patient and includes at least one aperture in the second portion for allowing fluid communication between the exterior of the catheter and the passageway. A housing includes a proximal end having a proximal opening, a distal end having a distal opening and a side wall therebetween defining a conduit in the housing. The catheter is positioned in the proximal opening and capable of passing through the distal opening. A catheter connector fitting on the housing is provided for connecting the first end of the catheter to the housing. A vacuum connector fitting is provided for facilitating fluid communication between the catheter connector and the source of vacuum so that when vacuum forces are applied through the vacuum connector fitting the vacuum forces are communicated to the passageway of the catheter. A flexible envelope is connected to the housing so that substantially all portions of the catheter between the catheter connector fitting and the proximal opening are within the envelope. The envelope is flexible enough to allow manual movement of the catheter through the distal opening by grasping the envelope adjacent to a portion of the catheter and manually moving the catheter.

30 Claims, 6 Drawing Sheets

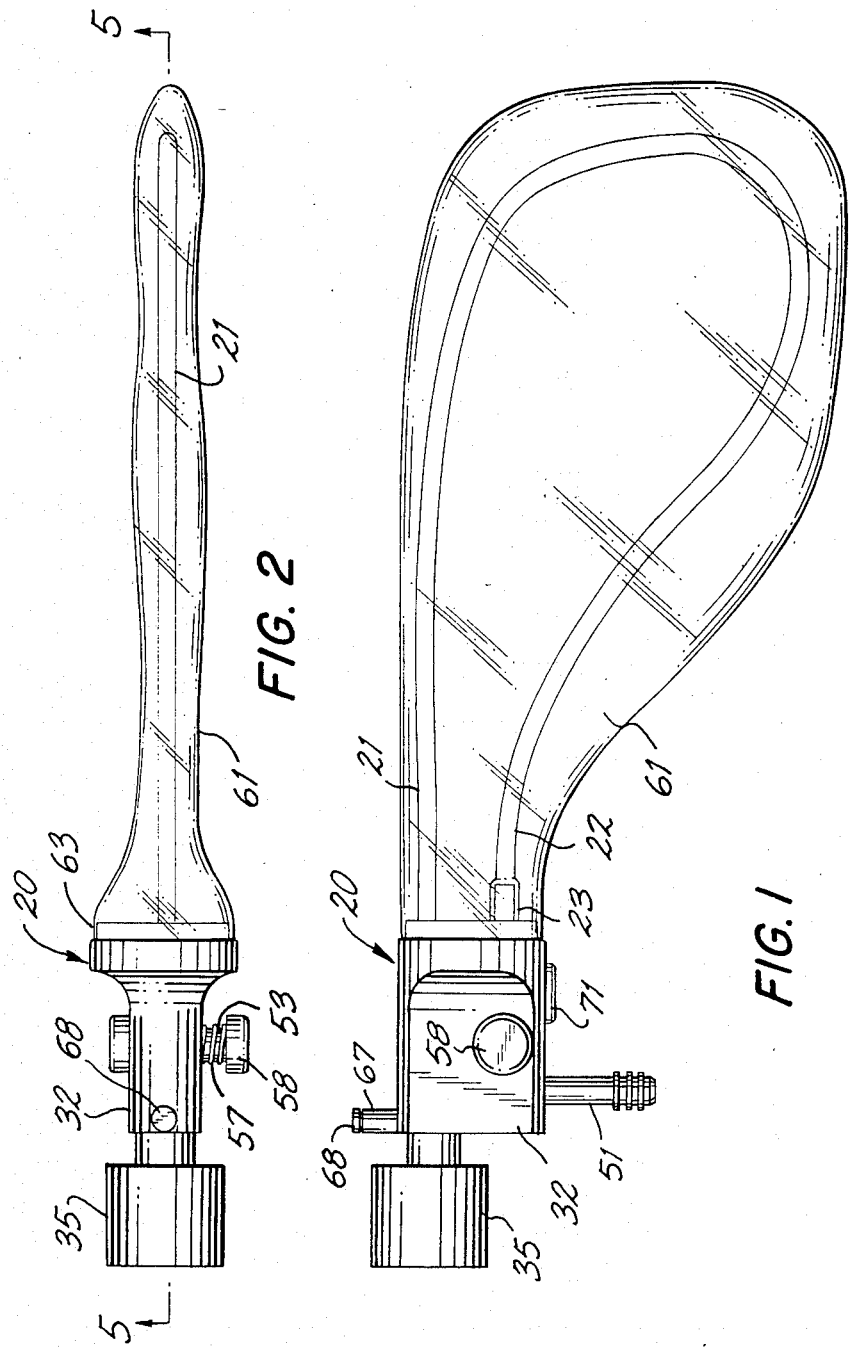

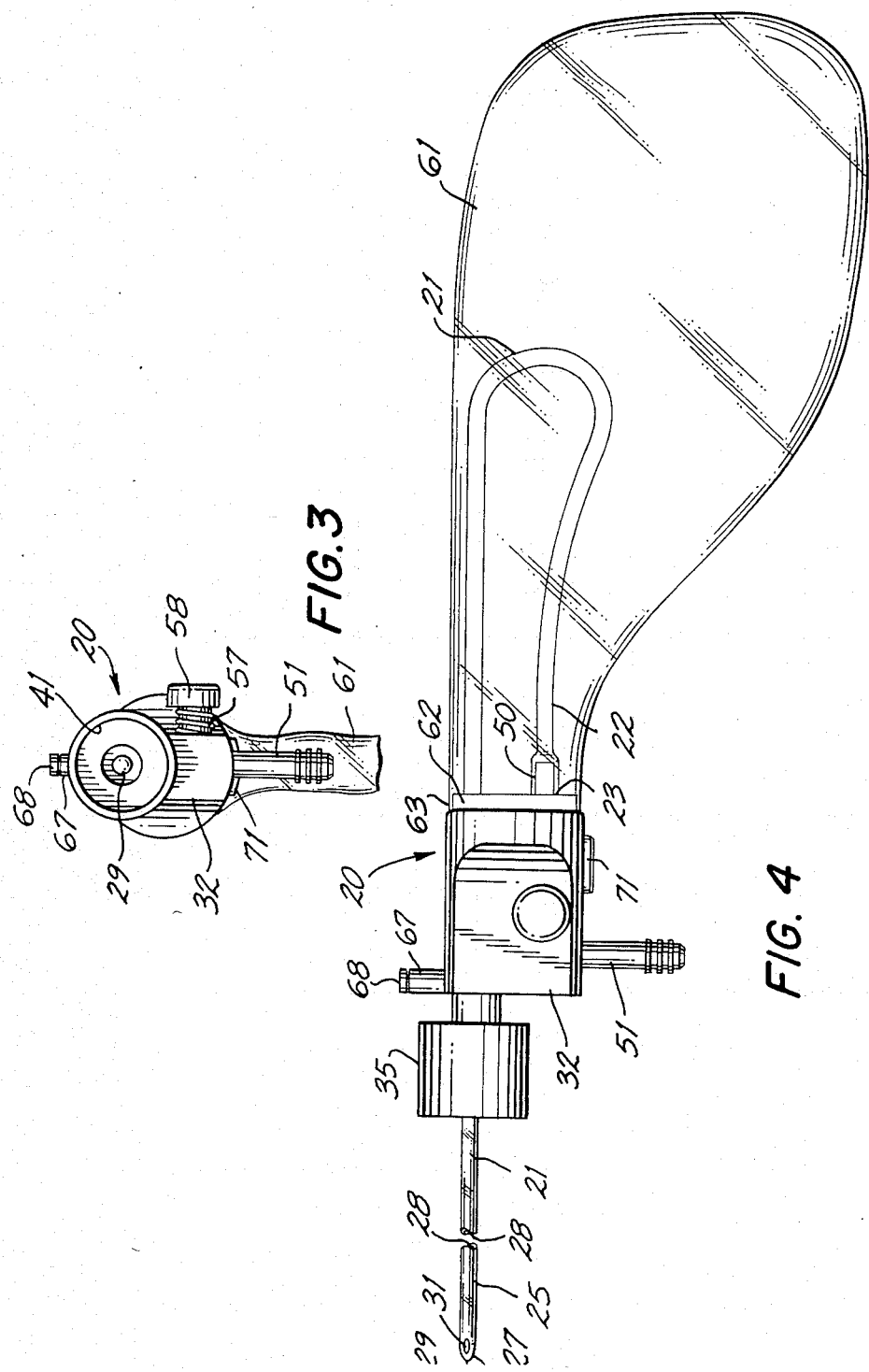

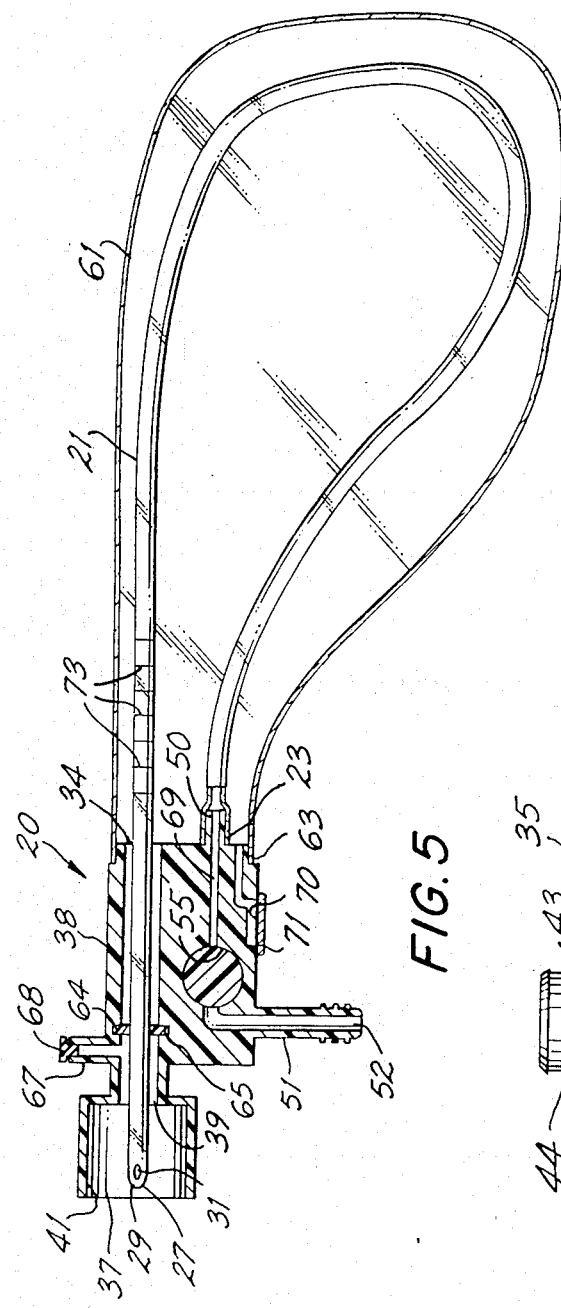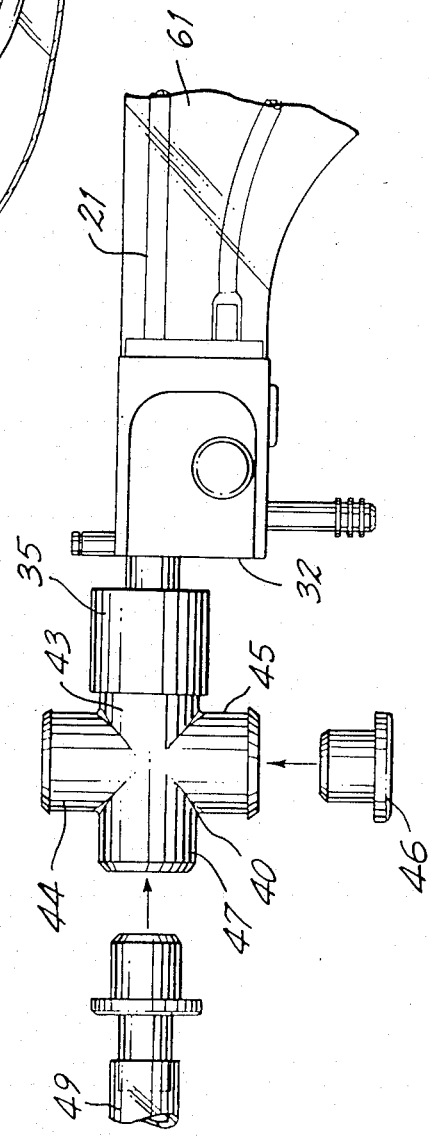

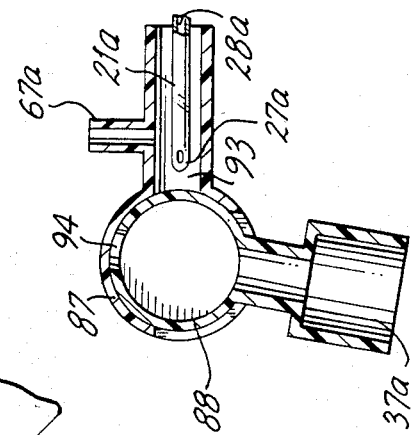
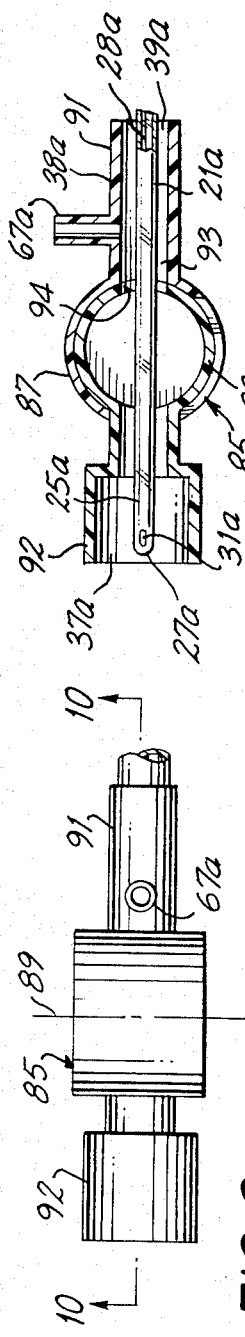
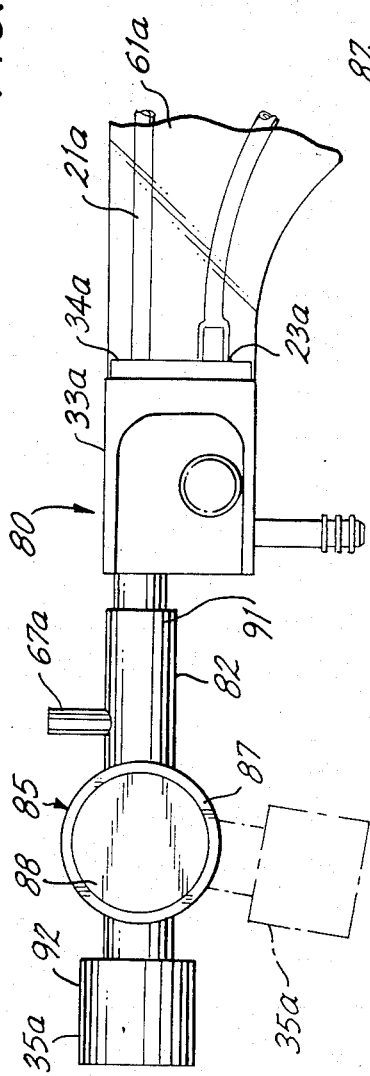
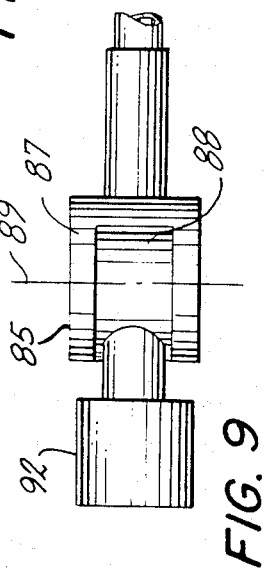

ASPIRATING DEVICE

BACKGROUND OF THE INVENTION

1. Field of the Invention

The present invention relates to an aspirating device for removing undesirable secretions from a mammalian body and more particularly concerns an aspirating device for use in suctioning undesirable secretions from the trachea of a patient.

2. Description of Related Information

Various forms of respiratory therapy require the use of a ventilator which is a device which provides for the movement of gases into and out of the pulmonary system. Usually a ventilator is used in conjunction with some form of arterial airway or tube which is inserted into the patient's trachea through the mouth (endotracheal tube) or into the patient's trachea through an incision in the patient's neck (tracheostomy tube). The tracheostomy procedure is sometimes preferred because it bypasses and therefore avoids complication with portions of the upper airway.

Artificial airways are established for adequately supporting ventilation for an extended period of time. The artificial airway also prevents a potential danger to the patient by diminishing the patient's ability to cough and to voluntarily remove undesirable secretions from the trachea. Accordingly, the removal of the secretions from a patient having a temporary artificial airway, for example, during therapy involving a ventilator, is affected by aspiration or suctioning. Patients with a substantial amount of secretions require frequent aspiration or suctioning to remove secretions from the trachea.

A known and available suctioning device is a suction catheter as described in U.S. Pat. No. 3,319,628 to Halligan. The suction catheter, as taught by Halligan, is connected to a source of vacuum and is inserted through the artificial airway and into the trachea of the patient wherein the suction forces draw secretions into the catheter and out of the trachea and the artificial airway. Halligan teaches an improved catheter having means for manual regulation of the vacuum forces. In particular, Halligan teaches a suction catheter comprising a flexible catheter having an opening at its distal end and a rigid regulator at its proximal end. The regulator includes a bore which is aligned with the lumen of the catheter and a second bore which is perpendicular to the fluid path of the catheter in the first bore. A finger engaging piece is associated with the regulator and includes a concave surface adapted to receive the finger of the user for occluding the secondary bore. The secondary bore acts as a bleed so that when it is not occluded, outside air enters the bore in the vacuum line and reduces the vacuum forces at the distal tip of the catheter to substantially zero while occluding the secondary bore with the finger terminates all bleed air and maximizes the vacuum forces at the tip of the catheter and partial occlusion will tend to provide vacuum forces between the two extremes. The catheter taught by Halligan provides an effective device for suctioning the trachea and the other body passageways. These suction catheters are simple in structure, maneuverable, easy to regulate with respect to suction forces and disposable. The disposability is believed to be a desirable feature because bacteria encountered in the patient's trachea is deposited on the exterior of the catheter and under certain circumstances will continue to grow and multiply. Also, after removal of the catheter from the patient, other airborne bacteria may contact the catheter and grow on its surface. Accordingly, reusing such an instrument is believed to be hazardous to the patient because it could introduce bacteria into the respiratory system. A similarly structured suction and oxygenation catheter is taught by Gandi et al. in U.S. Pat. No. 4,300,550.

Radford, in U.S. Pat. No. 3,991,762 teaches a reusable aspirating device for use with the patient ventilation apparatus. In one embodiment, Radford teaches an aspirating device consisting of a catheter tube and a protective housing. The protective housing includes a patient coupling element slidably positioned so as to surround the catheter tube nearest that end thereof suitable for insertion into the trachea and a vacuum coupling element mounted adjacent to the end of the catheter remote from the end adapted to be inserted into the trachea. A protective envelope extending between the patient coupling element and the vacuum coupling element is formed of a flexible plastic material which distorts and compresses when the vacuum coupling element and the patient coupling element are moved relatively toward one another. The patient coupling element also includes a seal surrounding the catheter tube, and adapted to help prevent fluid secretions located on the exterior surface of the catheter from being withdrawn into the envelope, and an irrigation port suitable for connection to an irrigation source and in communication with the external surface of the catheter tube. Radford teaches that the aspiration device should remain connected to the ventilation apparatus via the patient coupling element and that the same catheter can be reused many times by a single patient. Although the Radford aspirating device appears to be more expensive to manufacture it may be an improvement, with respect to cost, if several aspirating procedures can be performed with the same device which remains continuously connected to the ventilator during the patient therapy. Also, the apparatus taught by Radford, offers the advantage of being usable without disconnecting the ventilator so that it is not necessary to follow the procedure of pre-oxygenating the patient before using the suction catheter and a subsequent reoxygenating step after use of the suction catheter. In addition, the respiratory therapist using the device of Radford is not under the time pressure to perform the suctioning procedure in a minimal amount of time while the ventilator is disconnected.

An aspirating device substantially similar to the device of Radford is taught in U.S. Pat. No. 3,902,500 to Dryden. Dryden's aspirating device does not include a seal surrounding the catheter tube and an irrigation port in the patient coupling element.

U.S. Pat. Nos. 4,569,344 and 4,638,539 to Palmer teach what appear to be improvements to the Radford device regarding specific structures for the patient coupling element and a vacuum coupling element including a lockable vacuum control valve in the vacuum coupling element.

U.S. Pat. No. 4,691,702 to Chantzis teaches an aspirating device which in one embodiment includes a patient housing, a flexible catheter, a vacuum coupling housing at the proximal end of the catheter and a flexible sleeve surrounding a portion of the catheter. Unlike the aspirating devices of Radford, Dryden and Palmer, the aspirating device of Chantzis teaches a flexible sleeve which is contained within the patient housing and is not connected to the vacuum coupling housing so that any portion of the catheter or the sleeve which contacts secretions in the trachea of the patient cannot pass through the proximal end of the patient coupling housing thereby confining these surfaces to a specific protected area within the patient coupling housing.

Although the devices taught by Radford, Dryden and Palmer may provide some advantages over the prior art suction catheters, they still have disadvantages. Most notably, the vacuum connection housing, which usually contains a valve to control the vacuum forces, is a substantial distance from the patient coupling element and the patient's throat area. Since the catheter and the protective envelope are flexible the vacuum housing is free to move around and possibly become entangled with the patient bed frame or other adjacent apparatus so that further movement with respect to the patient can disconnect the elements of the catheter assembly and/or possibly cause patient trauma by applying forces to the endotracheal tube or tracheostomy tube. Also, inadvertent action by the patient or other party on the remote vacuum control valve may cause initiation of vacuum forces when they are not desired and may be detrimental to the patient. To avoid this problem Palmer, in U.S. Pat. No. 4,569,344, teaches a valve that may be manually locked in a closed position to prohibit inadvertent actuation of the valve. Also, this type of aspirating device requires the movement of the entire mass of the vacuum coupling element and associated valve whenever the catheter is moved along the trachea of the patient. In addition, when a shielded catheter is connected to a patient ventilating unit it is desirable not to have flow of the ventilation gases into the aspirating device which would be tantamount to a leak lowering the efficiency of the ventilation device. The teachings of the prior art do not appear to recognize this as a serious problem, however, the seal taught by Radford to remove secretions from the outside of the catheter would also be helpful in reducing the effect of the ventilator on the envelope so that the ventilator pressures cause the patient's lungs to expand and contract and not the catheter envelope.

Catheters and catheter assemblies for use in suctioning of the trachea and other passages in the patient's body, for use alone or with a ventilator, both disposable and reusable, have been addressed by the prior art. However, there is still a need for a simple, straight-forward, reliable, easily fabricated reusable aspirating device having an improved structure fixing the position of the vacuum coupling element and valve to minimize the potential for inadvertent actuation or inadvertent assembly and to allow movement of the catheter into and out of the patient's trachea without moving valves and other structural elements. It is also desirable to have a more effective seal between the ventilator and the aspirating device so that, while not in use, the ventilator does not force gases into the catheter sheath.

SUMMARY OF THE INVENTION

The operable aspirating device of the present invention, for use in removing undesirable secretions, includes a flexible catheter having a proximal first end, a distal second portion including a second end and a passageway therethrough. The catheter is adapted for insertion into the trachea of a patient and includes at least one aperture in its second portion for allowing fluid communication between the exterior of the catheter and the passageway. A housing includes a proximal end having a proximal opening, a distal end having a distal opening and a side wall therebetween defining a conduit in the housing. The catheter is positioned so that it passes through the proximal opening and is capable of passing through the distal opening. Catheter connector means is provided on the housing for connecting the first end of the catheter to the housing. Vacuum connector means for facilitating fluid communication between the catheter connector means and a source of vacuum is provided so that when vacuum forces are applied through the vacuum connector means the vacuum forces are communicated to the passageway of the catheter. A flexible envelope is connected to the housing so that substantially all portions of the catheter between the catheter connector means and the proximal opening are within the envelope. The envelope is flexible enough to allow manual movement of the catheter through the distal opening by grasping the envelope adjacent to a portion of the catheter and manually moving the catheter.

In a preferred embodiment of the present invention, an operable aspirating device for use in conjunction with a patient ventilation apparatus for removing undesirable secretions includes an elongate flexible catheter having a proximal first portion including a first end, a distal second portion including a second end and a passageway therethrough. The catheter is adapted for insertion into the trachea of a patient. The catheter includes at least one aperture in the second portion for allowing fluid communication between the exterior of the catheter and the passageway. A housing includes a proximal end having a proximal opening, a distal end having a distal opening and a side wall therebetween defining a conduit in the housing. The catheter is positioned within the proximal opening and capable of passing through the distal opening of the housing. The housing also includes means for connecting the housing to a patient ventilation apparatus. Catheter connector means is provided on the housing for connecting the first end of the catheter to the housing. Vacuum connector means is provided on the housing for facilitating fluid communication between the catheter connector means and the source of vacuum so that when vacuum forces are applied through the vacuum connector means the vacuum forces are communicated to the passageway of the catheter. Valve means is provided for regulating vacuum forces in the passageway and includes a manually operable valve in operative relation to the housing. A flexible envelope is connected to the housing so that substantially all portions of the catheter between the catheter connector means and the proximal opening are within the envelope. The envelope is flexible enough to allow manual movement of the second end of the catheter toward and away from the distal opening by grasping the envelope adjacent to a portion of the catheter and manually moving the catheter. Vent means is provided for venting gases from within the envelope when gas pressures within the envelope exceed atmospheric pressure by a pre-determined amount. Seal means is provided for restricting gas flow between the conduit in the housing and the exterior of the housing through the distal opening.

Another embodiment of the aspirating device of the present invention includes manually operable passageway valve means capable of occluding the passageway when the second end of the catheter is positioned proximally of the valve means for preventing fluid communication between the flexible envelope and the ventilation apparatus while the catheter is not being used for removing secretions.

In another embodiment of the aspirating device of the present invention the housing side wall includes a collapsible, flexible, bendable, sleeve defining a portion of the passageway of the housing. The sleeve is capable of expanding to move the distal end of the housing and the proximal end of the housing further apart. Means is provided for releasably holding the sleeve in a collapsed position.

In accordance with the principles of the present invention a number of advantages are achieved. Primarily, the present invention provides a simple, straight-forward, reliable, easily fabricated aspirating device which may be used in conjunction with the ventilation system on the same patient without disposal of the aspiration device between successive uses. The instant invention also provides a unique structure which fixes the position of the vacuum coupling element and valve to minimize the potential for inadvertent actuation and inadvertent disassembly, and to allow movement of the catheter into and out of the patient's trachea without moving valves and other structural elements. An alternative embodiment of the instant invention also provides a more effective seal between the ventilator and the aspirating device so that, while not in use, the ventilator does not force gases into the catheter sheath.

BRIEF DESCRIPTION OF THE DRAWINGS

FIG. 1 is a side elevation view of the aspirating device of the present invention;

FIG. 2 is a top plan view of the aspirating device of FIG. 1

FIG. 3 is a front elevation view of the aspirating device of FIG. 1;

FIG. 4 is another side elevation view of the aspirating device of the present invention illustrating the catheter in a partially advanced position so that the second end of the catheter protrudes from the housing:

FIG. 5 is a partial cross-sectional view of the aspirating device of FIG. 2 taken along lines 5—5;

FIG. 6 is a side elevation exploded view of the aspirating device of the present invention illustrated with portions of a patient ventilating system:

FIG. 7 is a partial side elevation view of an alternative embodiment of the aspirating device of the present invention;

FIG. 8 is a partial top plan view of the aspirating device of FIG. 7;

FIG. 9 is a partial bottom plan view of the aspirating device of FIG. 7:

FIG. 10 is a cross-sectional view of the aspirating device of FIG. 8 taken along line 10—10:

FIG. 11 is a cross-sectional view similar to the cross-sectional view of FIG. 10 with the passageway valve illustrated in a passageway occluding position:

DETAILED DESCRIPTION

Figure 12:
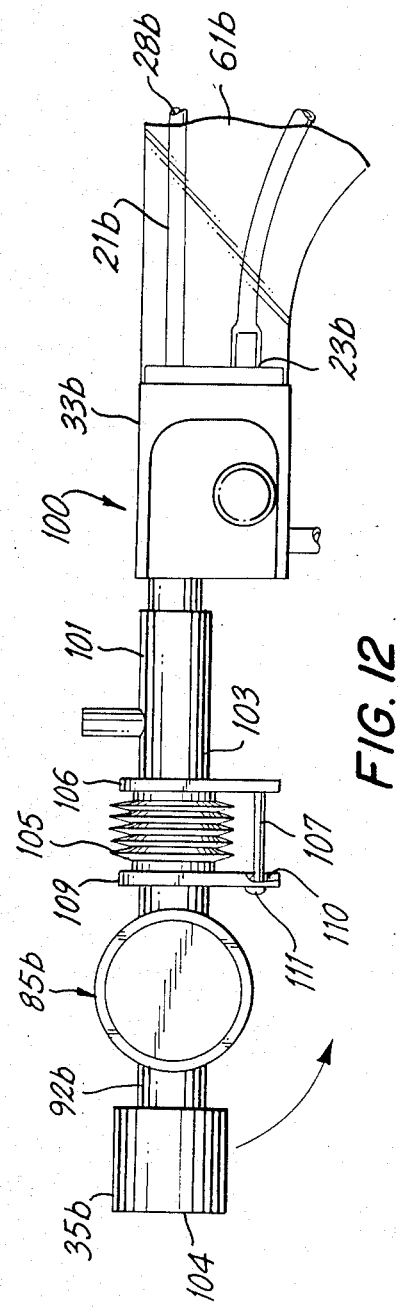
FIG. 12 is a partial side elevation view of still another alternative embodiment of the present aspirating device wherein the housing includes a compressible sleeve.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1-6, an operable aspirating device 20 for use in conjunction with a patient ventilation apparatus for removing undesirable secretions includes an elongate flexible catheter 21 having a proximal first portion 22, including a first end 23, a distal second portion 25 including second and 27 and a passageway 28 therethrough. For the purposes of the description of the present invention, the term "distal" is generally meant to refer to that end of the aspirating device which is furthest from the person holding the aspirating device, whereas the term "proximal" is generally meant to refer to the end of the aspirating device closest to the holder of the device.

The catheter is adapted for insertion through a portion of a ventilating apparatus, to be described in more detail hereinafter, and into the trachea of a patient. To facilitate insertion into the trachea, the distal end of the catheter should preferably be formed so that, wherever possible, the edges are gently rounded to facilitate smooth insertion. One way to achieve this end is to provide a rounded, convexly-shaped closed end 29 on the catheter and at least one aperture 31 in distal second portion 25, in the catheter side wall, for allowing fluid communication between the exterior of the catheter and passageway 28. It is within the purview of the instant invention to include catheters of a wide variety of lengths and diameters. A desirable catheter length is about 560 mm long having an outside diameter of approximately 4.7 mm. However, the choice of catheter length and diameter will be influenced by compatibility with other devices being used with the catheter and, more importantly, by accepted medical standards for the procedure being performed.

A housing 32 includes a proximal end 33 having a proximal opening 34, a distal end 35 having a distal opening 37 and a side wall 38 therebetween defining a conduit 39 in the housing.

Catheter 21 passes through proximal opening 34 and, in this preferred embodiment is capable of passing through distal opening 37. It is desirable to produce the catheter assembly so that second end 27 of the catheter can be withdrawn into the housing 32 so that the catheter does not project into the ventilator air passageway when it is not in use, and so that the catheter tip will be protected between uses and/or during shipping. However, this structure is merely preferred and not necessary and a functional aspirating device can be made where, even in the retracted position, catheter 21 protrudes through distal opening 37 of the housing.

Housing 32 includes means for connecting the housing to a patient ventilation apparatus so that the catheter may enter the patient ventilation apparatus through distal opening 37. As best illustrated in FIG. 6, cross-shaped connector 40 of a ventilating apparatus, which will be explained in more detail hereinafter, is capable of joining the aspirating device via the slight interference fit between inside diameter 41 at distal opening 37 of the housing passageway and the outside diameter of the cross-shaped ventilator connector at port 43. Port 44 of cross-shaped connector 40 is provided for communication with a portion of the ventilator apparatus which provides the desired gas mixture for patient respiration. Port 45 which is normally sealed by plug 46 is provided for communication with additional apparatus. Port 47 is adapted for connection to an endotracheal tube or a tracheostomy tube 49 having a distal end (not shown) positioned in the trachea of a patient. It is also within the purview of the instant invention to include embodiments wherein the port provided for communication with a portion of the ventilator apparatus, similar to port 44, is integrally formed with or connected directly to the housing so that the distal end of the housing connects directly with the tracheostomy tube or endotracheal tube. Also, additional ports, such as port 45, may be integrally formed with or connected directly to the housing rather than being part of a separate connector or adapter.

Catheter connector means is provided on the housing for connecting the first portion on the first end of the catheter to the housing. In this embodiment, the catheter connector means includes a tubular fitting 50 projecting outwardly from proximal end 33 of the housing. In this embodiment, the outside diameter of tubular fitting 50 is larger than the inside diameter of catheter 21 so that first end 23 of the catheter may be forced over the tubular fitting and held there by virtue of the interference fit. The inner section between the first end of the catheter and the catheter connecting means can be secured by adhesive, ultrasonic welding, clamping or any suitable means with the construction illustrated herein being exemplary of these many possibilities.

Vacuum connector means is provided for facilitating fluid communication between the catheter connector means and a source of vacuum (not shown) so that when vacuum forces are applied through said vacuum connector means the vacuum forces are communicated to passageway 28 of the catheter. In this embodiment the vacuum connector means includes tubing fitting 51 having a tubular duct 52 extending through housing 32 to fitting 50.

In this preferred embodiment vacuum valve means is provided for regulating vacuum forces in passageway 28. In this preferred embodiment the vacuum valve means includes a manually operable, normally closed valve consisting of valve stem 53 positioned in bore 55 which runs across the housing interrupting tubular duct 52. Valve stem 53 is held in the movable normally closed position by coil spring 57. Valve stem 53 also includes a drill hole (not shown) running perpendicular to its longitudinal axis and positioned so that when digital pressure is applied to cap 58 of the valve stem, compressing coil spring 57, the drill hole will move into alignment with tubular duct 52 allowing the vacuum forces to communicate directly through passageway 28 of catheter 21. The vacuum forces may be modulated by moving the valve stem through various positions by applying digital pressure. It will be apparent to one skilled in the art that numerous valve constructions can be used to regulate vacuum forces in a tubular duct, including various valve types and mechanisms using resilient tubing carrying the vacuum which may be compressed by an externally applied force and the like. The above described valve is intended to be exemplary of these many possibilities. It is also within the purview of this invention to include the aspirating device without a valve attached or within the housing wherein the user may rely on regulating the source of vacuum or regulating the vacuum between the vacuum source and the housing of the the aspirating device.

A flexible envelope 61 is connected to the housing so that substantially all portions of the catheter between the catheter connector means (tubular fitting 50) and proximal opening 34 of the housing are within the envelope. The envelope is flexible enough to allow manual movement of second end 27 of the catheter toward and away from distal opening 37 of the housing by grasping the envelope adjacent to a portion of the catheter and manually moving the catheter. In this preferred embodiment, housing 32 includes a raised boss 62 at proximal end 33 of the housing wherein tubular fitting 50 and proximal opening 34 are within the periphery of the raised boss. Envelope 61 is closed on all sides except at its distal end 63 wherein it is attached to the outside of raised boss 62 using adhesive, heat sealing, ultrasonic welding or other suitable means. There are numerous constructions for sealing a flexible envelope to a rigid housing including manually camping the envelope to the housing or using threaded members to clamp a portion of the envelope to the housing and the like and the structure taught hereinabove incorporating raised boss 62 is representative of these many possibilities.

Seal means is provided for restricting gas flow between conduit 39 of the housing and the exterior of the housing through distal opening 37. In this preferred embodiment seal means includes resilient circularly shaped seal 64 contained in said housing conduit by seal groove 65. The inside diameter of resilient seal 64 contacts the outside of catheter 21 to help restrict gas flow from the ventilating apparatus to the interior of envelope 61 and to wipe undesirable secretions from the surface of catheter 21 as it is being withdrawn from the trachea of the patient back into the flexible envelope.

The preferred embodiment of the instant invention includes an irrigation port 67 in housing 32. The irrigation port is provided to allow fluid communication between the exterior of the housing and the exterior of catheter 21 so that irrigating fluid can be externally provided for flushing over the exterior of the flexible catheter to help remove undesirable secretions on the catheter which have accumulated during a suctioning procedure. Ideally, these fluids will wash the secretions toward distal end 27 of the catheter wherein they will be drawn through aperture 31 and through the passageway of the catheter, toward the vacuum source. Irrigation port 67 is normally occluded by movable plug 68, which can be removed to allow irrigation and replaced after the irrigation procedure. It is also within the purview of the instant invention to provide an irrigation port which is occluded by a fixed pierceable septum wherein irrigation fluid can be provided by injection with a hypodermic syringe having a sharpened needle for piercing the septum.

It may be desirable to provide vent means for venting gases within the envelope when gas pressures within the envelope exceed atmospheric pressure by a pre-determined amount. Gases which may be forced from the patient ventilation system through the interface of catheter 21 and seal 64 may cause the flexible envelope to expand making it more difficult to comfortably move the catheter. Also, the gas pressures may stress the envelope undesirably. In the preferred embodiment vent means is provided by a venting conduit 69 which provides for communication between the proximal end of the housing, within the raised boss, and aperture 70 in the side wall of housing 32. A filter element 71 is connected to the housing covering aperture 70 so that all gases passing through venting conduit 69 must pass through filter element 71. In this embodiment filter element 71 is preferably made of porous material having a maximum pore rating of about 0.5 micron for serving as a substantial barrier to particles about 0.5 micron and larger. The filter element may be attached to the housing using adhesives, heat sealing or other suitable means. It is also within the purview of the instant invention to construct the filter element out of a three-dimensional plug made of filter material which may be positioned within the venting conduit. Vent means may also include a one-way valve associated with the venting conduit positioned so that gases may leave the housing through the venting conduit but may not enter by virtue of the one-way action of the valve. Various suitable one-way valves are known such as an elastomeric duckbill valve. Also, vent means may include an aperture in the side wall of the envelope (not shown) covered by a filter element (not shown).

The aspirating device may also include measuring indicia 73 on catheter 21 positioned so that the user can estimate the distance between second end 27 of the catheter and the housing. Measuring indicia are a desirable feature for allowing the user to estimate how far the distal end of the catheter has penetrated the patient's trachea. If a transparent material is chosen for the envelope the indicia can be read through the envelope as the catheter moves through the housing. If the envelope is not transparent a viewing window (not shown) may be provided in the housing for reading the indicia.

FIGS. 7-11 illustrate an alternative embodiment of the aspirating device of the present invention further including manually operable passageway valve means. In this alternative embodiment the structure of the aspirating device is substantially identical to the embodiments of FIGS. 1-6. Accordingly, substantially similar components performing substantially similar functions will be numbered identically to those components in the embodiments of FIGS. 1-6, except a suffix "a" will be used to identify these components in FIGS. 7-11.

An operable aspirating device 80, of this embodiment, for removing undesirable secretions comprises a flexible catheter 21a having a proximal first end 23a, a distal second portion 25a including a second end 27a and a passageway 28a therethrough. The catheter includes at least one aperture 31a in the second portion for allowing fluid communication between the exterior of the catheter and the passageway. A housing 82 includes a proximal end 33a having a proximal opening 34a, a distal end 35a having a distal opening 37a and a side wall 38a therebetween defining a conduit 39a in the housing. The catheter passes through the proximal opening and is capable of passing through the distal opening of the housing. Housing 82 includes means for connecting the housing to a patient ventilator apparatus through the distal opening. Housing 82 includes a manually operable passageway valve 85 comprising two concentric contacting cylindrically-shaped or curved valve members, referred to herein as proximal cylindrically-shaped or curved valve member 87 and distal cylindrically-shaped or curved valve member 88. The concentric curved valve members have an axis of rotation 89 dividing housing 82 into a proximal housing portion 91 and a distal housing portion 92. Proximal curved valve member 87 includes proximal passageway 93 and distal curved valve member 88 includes distal passageway aperture 94 wherein both passageway apertures are aligned with passageway 39a. Passageway 39a may be bent at axis 89 by manually rotating distal housing portion 92 with respect to proximal housing portion 91 along axis 89 as illustrated in FIG. 12. When the housing portions are rotated with respect to each other along axis 89 one of the passageway apertures is covered or blocked or occluded by the curved member of the other passageway aperture. In this embodiment, as illustrated in FIG. 11, distal curved valve member 88 covers proximal passageway aperture 93. When valve 85 is in the off position as illustrated in FIG. 11, it acts to prevent fluid communication between the flexible envelope 61a and the ventilation apparatus (not shown) while the catheter is not being used for removing secretions. It should be noted that it is within the purview of the instant invention to position the axis of rotator of the passageway valve at an orientation which is perpendicular to the orientation of axis 89 so that the distal housing portion moves side-to-side with respect to the proximal end of the housing rather than up and down as illustrated in FIGS. 7-11, or at any angle therebetween.

Manually operable passageway valve 85 is an important feature of this embodiment in that it acts as a positive barrier for isolating the catheter and the flexible envelope from the pressurized gases in the ventilation apparatus while the catheter is not being used for suctioning. Accordingly, gases intended for patient therapy are not bled off or inadvertently transferred to the envelope. In addition, as will be explained in more detail hereinafter, proper design of the passageway valve will allow positioning the aspiration device in a more comfortable position with respect to the patient while it is not in use. It will be apparent to one skilled in the art that numerous valve structures, such as gate valves and the like, can be used as a valve means to occlude the passageway of the housing and that the manually operable passageway valve of FIGS. 7-11 is representative of these many possibilities. These other valve structures are within the purview of the instant invention.

It should be noted, in this embodiment irrigation port 67a is positioned closer to the distal end of the housing than in the embodiment of FIGS. 1-6. The more distal position in this embodiment allows the user to occlude the passageway using the valve as illustrated in FIG. 11 and then, with the catheter positioned as in FIG. 11, introduce irrigating fluid over the tip of the catheter to clean that portion of the catheter wherein the fluid may be drawn through the catheter as in normal suctioning procedures.

Figure 13:
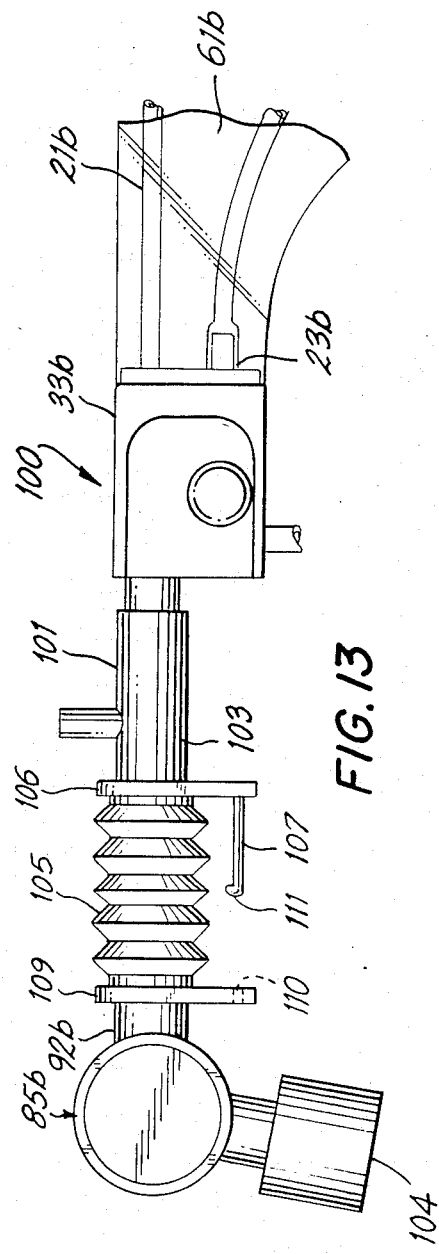
FIG. 13 is another partial side elevation view of the aspirating device of FIG. 12 illustrating the sleeve in an expanded position.
Figure 15:
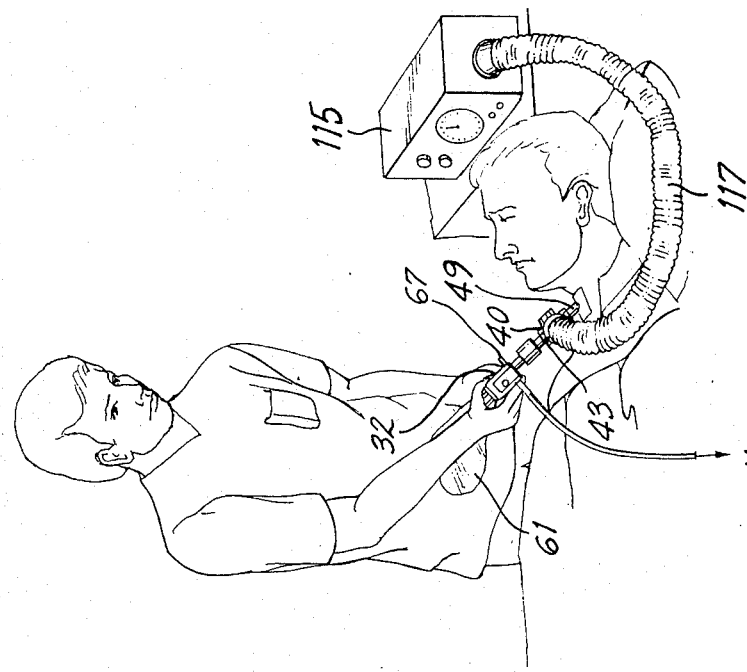
FIG. 15 is a perspective view illustrating the aspirating device of the present invention being used in patient therapy.
Figure 14:
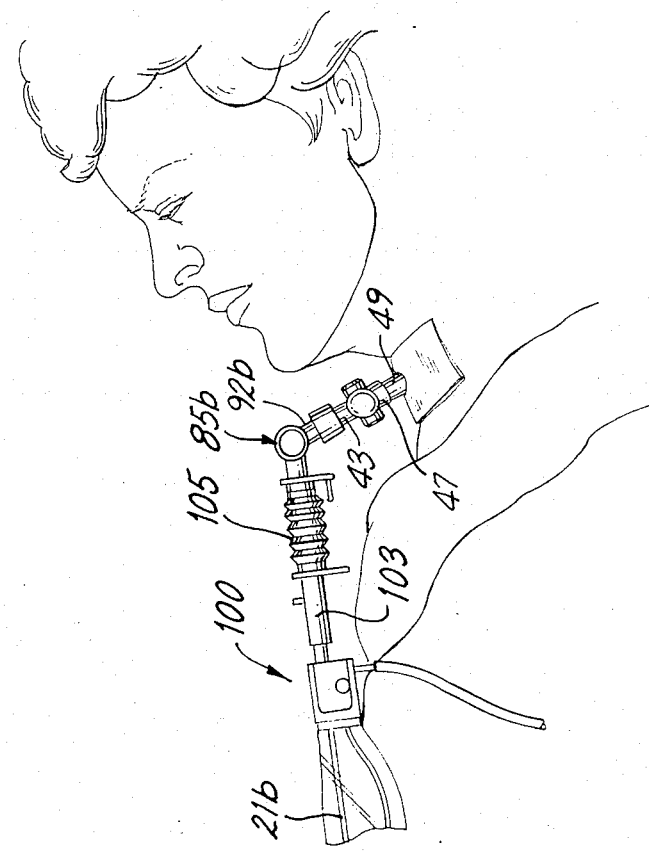
FIG. 14 is a partial side elevation view illustrating the aspirating device of FIGS. 12 and 13 connected to a patient through a tracheostomy tube.

FIGS. 12-14 illustrate another alternative embodiment of the aspirating device of the present invention wherein the housing includes a collapsible sleeve. In this alternative embodiment the structure of the aspirating device is substantially identical to the aspirating device of FIGS. 7-11. Accordingly, substantially similar components performing substantially similar functions will be numbered identically to those components in the embodiment of FIGS. 7-11, except a suffix "b" will be used to identify these components in FIGS. 12-14. An operable aspirating device 100 of this alternate embodiment includes an elongate flexible catheter 21b having a proximal first end 23b and a distal second portion including a second end and a passageway 28b therethrough. A housing 101 includes manually operable passageway valve 85b dividing the housing into a proximal housing portion 103 and a distal housing portion 92b. Housing 101 includes passageway 104 extending from distal end 35b to proximal end 33b. Proximal housing portion 103 includes a collapsible, flexible, bendable, sleeve 105 defining a portion of the passageway positioned between valve 85b and proximal end 33b. Sleeve 105 is capable of expanding to move distal end 35b and proximal end 33b further apart. Means is provided for releasably holding sleeve 105 in a collapsed position. In this embodiment means for releasably holding the sleeve in a collapsed position includes flange 106 on the proximal side of the sleeve including engaging pin 107, and flange 109 on the distal side of the sleeve including pin receiving aperture 110. In this embodiment the sleeve is made of bendable thermoplastic material such as polypropylene. The sleeve may be collapsed by forcing the portions of the housing on either side of the sleeve toward one another so that engaging pin passes through pin receiving aperture and latch portion 111 of the pin hooks onto the distal side of flange 109 holding the assembly tightly together as illustrated in FIG. 13. In fabricating the housing of the instant embodiment it may be desirable to mold the flanges as part of adjacent housing structure and then attach flexible sleeve 105 to the housings using adhesive, heat sealing, ultrasonic welding or other suitable means. Although the accordion-shaped structure of sleeve 105 is preferred, other collapsible sleeve structures are within the purview of this invention. An important advantage of this embodiment is that when the aspirating device is not being used in suctioning procedures pin 110 can be disengaged from flange 109 and sleeve 105 stretched slightly so that it will be moved a short distance away from the patient's throat and chin area making it more comfortable for the patient by allowing a portion of the aspirating device assembly to rest on the patient's chest. As best illustrated in FIG. 14, the manually operable passageway valve and the collapsible sleeve can be designed to work together to move a substantial portion of the aspirating device assembly out of the area of the patient's throat and neck and onto the patient's chest but not a substantial distance away as in some prior art devices. It is also within the purview of the instant invention to position the collapsible, flexible, bendable sleeve between valve 85b and the distal end of the housing rather than between valve 85b and the proximal end of the housing as illustrated in FIGS. 7-11. Although the collapsible sleeve is shown in conjunction with the passageway valve it is within the purview of this invention to include embodiments wherein the collapsible flexible bendable sleeve will be used in conjunction with an aspirating device not having a manually operable passageway valve such as the embodiment of FIGS. 1-6.

Referring now to FIGS. 1-15, in use the aspirating device of the instant invention can be attached to a patient ventilation apparatus which includes a source of pressurized oxygen 115 delivering the oxygen through conduit 117 into port 44 of cross-shaped connector 40 which is connected to, for example, a tracheostomy tube which is partially positioned in the patient's trachea. From time to time during the ventilation procedure it will become necessary to remove undesirable secretions from the patient's trachea. The aspiration device of the instant invention may be used in performing an aspiration or suctioning procedure to remove the secretions. Because the aspiration device is connected to the ventilator via port 43 it is not necessary to disconnect the ventilator from the patient. To perform an aspirating procedure, the respiratory therapist may activate a source of vacuum V and provides sterile irrigation liquid for irrigation through irrigation port 67 of the housing before advancing the catheter into the patient's trachea. The catheter may be advanced by grasping the envelope of the aspirating device adjacent to a portion of the catheter and manually moving the catheter into the patient's trachea. An advantage of the instant invention over the prior art is that when the catheter moves into and out of the patient's trachea only the catheter and portions of the envelope are in motion. No housing is moved and the mass of the housing is not dragged along with the catheter during the procedure. It is believed that this is an advantage which makes it easier for the respiratory therapist to effectively manipulate the catheter in the patient's trachea. The other hand of the respiratory therapist may be used to hold housing 32 and manipulate the valve stem to vary the vacuum forces within the catheter passageway. The second end of the catheter can be advanced through distal opening of the housing through the ports of the cross-shaped connector and through the tracheostomy tube. At the end of the procedure, it may be desirable to inject more sterile irrigating fluid through the irrigation port while withdrawing the catheter in a proximal direction out of the ventilator system. The catheter may now remain in place until the next aspirating procedure. With embodiments containing a manually operable passageway valve the valve may then be placed in the shut position to provide a positive barrier between the pressurized gases of the ventilator system and the envelope. If the manually operable valve is of the type illustrated in FIGS. 7-11 then it should be bent in an orientation to move a portion of the aspirating device to a more comfortable position away from the patient's chin toward the patient's chest. At this time, if the embodiment includes a collapsible sleeve, the sleeve should be expanded to move portions of the aspirating device away from the tracheostomy tube and to rest them on the patient's chest.

Porous filter material, such as filter element 71, can be made of non-woven polymeric fabrics such as polytetrafluoroethylene, polyester, polyvinylchloride, polypropylene, polyethylene and the like, preferably ranging in thickness of from about 0.003 to 0.010 inches (0.08 to 0.25 mm). Such materials as just described are available from W. L. Gore and Associates, Inc. of Elkton, Md., and are sold as GORE-TEX membrane products. The preferred element has a maximum pore rating of 0.5 micron for serving as a substantial barrier to particles about 0.5 micron and larger.

A wide variety of flexible materials are suitable for forming the catheter with thermoplastic material such as polyvinylchloride and polyethylene being preferred. A wide variety of rigid materials can be used in forming the rigid portions of the housing and valve means with rigid thermoplastic materials such as polystyrene, polyethylene, polyvinylchloride being preferred.

A wide variety of flexible materials are suitable for forming the flexible envelope either transparent, translucent or light impervious. Such materials as natural rubber, synthetic rubber and thermoplastic materials are possible with a thin membrane structure using polymeric materials such as polytetrafluoroethylene, polyester, polyvinylchloride, polypropylene and polyethylene being preferred. It is preferred that all elements of the aspirating device of the instant invention be sterile when used. Accordingly, a material should be selected for compatibility with the sterilization process being used.

Thus it can be seen that the present invention provides a simple, straight-forward, reliable, easily fabricated aspirating device which may be used in conjunction with a ventilation system and having an improved structure fixing the position of the vacuum coupling element and valve to minimize the potential for inadvertent actuation or inadvertent disassembly, and to allow movement of the catheter into and out of the patient's trachea without moving valves and other structural elements. An alternative embodiment of the present invention also provides a more effective seal between the ventilator and the aspirating device so that, while not in use, the ventilator does not force gases into the catheter sheath. Another alternative embodiment of the present invention provides a collapsible, flexible sleeve which allows a portion of the aspirating device to be moved away from the patient's throat to improve comfort while the catheter is not being used in suctioning procedures.

What is claimed is:

1. An operable aspirating device for use in conjunction with a patient ventilation apparatus for removing undesirable secretions comprising:
    an elongate flexible catheter having a proximal first portion including a first end, a distal second portion including a second end and a passageway therethrough, said catheter being adapted for insertion into the trachea of a patient, said catheter having at least one aperture in said second portion for allowing fluid communication between the exterior of said catheter and said passageway,
    a housing including a proximal end having a proximal opening, a distal end having a distal opening and a side wall therebetween defining a conduit in said housing, said catheter passing through said proximal opening and capable of passing through said distal opening, said housing including means for connecting said housing to a patient ventilation apparatus;
    catheter connector means on said housing for connecting said first portion of said catheter to said housing:
    vacuum connector means for facilitating fluid communication between said catheter connector means and a source of vacuum, so that when vacuum forces are applied through said vacuum connector means the vacuum forces are communicated to said passageway of said catheter; and
    a flexible envelope connected to said housing so that substantially all portions of said catheter between said catheter connector means and said proximal opening are within said envelope, said envelope being flexible enough to allow manual movement of said second end of said catheter toward and away from said distal opening by grasping said envelope adjacent to a portion of said catheter and manually moving said catheter.

2. The aspirating device of claim 1 further including vacuum valve means for regulating the vacuum forces in said passageway.

3. The aspirating device of claim 2 wherein said vacuum valve means includes a manually operable valve in operative relation to said housing.

4. The aspirating device of claim 1 further including vent means for venting gases from within said envelope when gas pressures within said envelope exceed atmospheric pressure by a predetermined amount.

5. The aspirating device of claim 4 wherein said vent means includes a one-way valve.

6. The aspirating device of claim 4 wherein said vent means includes an air permeable filter made of porous filter material.

7. The aspirating device of claim 6 wherein the porous filter material has a maximum pore rating of 0.5 micron for serving as a substantial barrier to particles about 0.5 micron and larger.

8. The aspirating device of claim 6 wherein said envelope includes an aperture and said filter is mounted to occlude said aperture so that all gases passing through said aperture must pass through said filter.

9. The aspirating device of claim 6 wherein said vent means includes a conduit in said housing providing fluid communication between the interior of said envelope and the exterior of said housing, said filter being mounted to occlude said conduit so that all gases passing through said conduit must pass through said filter.

10. The aspirating device of claim 1 further including seal means for restricting gas flow between said conduit in said housing and the exterior of said housing through said distal opening.

11. The aspirating device of claim 10 wherein said seal means includes a seal connected to said housing in said conduit and surrounding said catheter.

12. The aspirating device of claim 1 wherein said housing includes an irrigation port for allowing fluid communication between the exterior of said housing and the exterior of said catheter for irrigation of said catheter.

13. The aspirating device of claim 1 wherein said second end of said catheter is closed.

14. The aspirating device of claim 1 wherein said catheter connector means includes a tubular fitting projecting outwardly from said proximal end of said housing.

15. The aspirating device of claim 14 further including a raised boss on said proximal end of said housing wherein said tubular fitting and said proximal opening are within the periphery of said raised boss, said envelope being attached to said boss.

16. The aspirating device of claim 1 further including measuring indicia on said catheter positioned so that the user can estimate the distance between said second end of said catheter and said housing.

17. The aspirating device of claim 1 wherein said envelope is transparent.

18. The aspirating device of claim 1 wherein said envelope is made from materials selected from the group consisting of natural rubber, synthetic rubber and thermoplastic materials.

19. The aspirating device of claim 1 wherein said envelope includes a thin membrane.

20. The aspirating device of claim 14 wherein said membrane is made of polymeric material selected from the group consisting of polytetrafluoroethylene, polyester, polyvinylchloride, polypropylene and polyethylene.

21. An operable aspirating device for removing undesirable secretions comprising:
    a flexible catheter having a proximal first end, a distal second portion including a second end and a passageway therethrough, said catheter being adapted for insertion into the trachea of a patient, said catheter having at least one aperture in said second portion for allowing fluid communication between the exterior of said catheter and said passageway, a housing including a proximal end having a proximal opening, a distal end having a distal opening and a side wall therebetween defining a conduit in said housing, said catheter passing through said proximal opening and capable of passing through said distal opening;

catheter connector means on said housing for connecting said first end of said catheter to said housing;

vacuum connector means for facilitating fluid communication between said catheter connector means and a source of vacuum, so that when vacuum forces are applied through said vacuum connector means the vacuum forces are communicated to said passageway of said catheter; and a flexible envelope connected to said housing so that substantially all portions of said catheter between said catheter connector means and said proximal opening are within said envelope, said envelope being flexible enough to allow manual movement of said catheter through said distal opening by grasping said envelope adjacent to a portion of said catheter and manually moving said catheter.

22. An operable aspirating device for use in conjunction with a patient ventilation apparatus for removing undesirable secretions comprising:

an elongate flexible catheter having a proximal first portion including a first end, a distal second portion including a second end and a passageway therethrough, said catheter being adapted for insertion into the trachea of a patient, said catheter having at least one aperture in said second portion for allowing fluid communication between the exterior of said catheter and said passageway, a housing including a proximal end having a proximal opening, a distal end having a distal opening and a side wall therebetween defining a conduit in said housing, said catheter passing through said proximal opening and capable of passing through said distal opening, said housing including means for connecting said housing to a patient ventilation apparatus;

catheter connector means on said housing for connecting said first end of said catheter to said housing;

vacuum connector means for facilitating fluid communication between said catheter connector means and a source of vacuum, so that when vacuum forces are applied through said vacuum connector means the vacuum forces are communicated to said passageway of said catheter;

valve means for regulating the vacuum forces in said passageway including a manually operable valve in operative relation to said housing:

a flexible envelope connected to said housing so that substantially all portions of said catheter between said catheter connector means and said proximal opening are within said envelope, said envelope being flexible enough to allow manual movement of said second end of said catheter toward and away from said distal opening by grasping said envelope adjacent to a portion of said catheter and manually moving said catheter;

vent means for venting gases from within said envelope when gas pressures within said envelope exceed atmospheric pressure by a predetermined amount; and seal means for restricting gas flow between said conduit in said housing and the exterior of said housing through said distal opening.

23. The aspirating device of claim 22 further including an irrigation port for allowing fluid communication between the exterior of said housing and the exterior of said catheter for irrigation of said catheter.

24. The aspirating device of claim 1 wherein said housing includes manually operable passageway valve means capable of occluding said passageway when said second end of said catheter is positioned proximally of said valve means for preventing fluid communication between said flexible envelope and the ventilation apparatus while said catheter is not being used for removing secretions.

25. The aspirating device of claim 24 wherein said passageway valve means comprises two concentric curved members having an axis of rotation which crosses said passageway dividing the said housing into a proximal housing portion and a distal housing portion, said concentric curved member including passageway apertures aligned with said passageway wherein one of said passageway apertures in one of said curved members may be occluded by the other of said curved members when said housing portions are rotated with respect to each other along said axis.

26. The aspirating device of claim 24 wherein said housing side wall includes a collapsible, flexible, bendable, sleeve defining a portion of said passageway, said sleeve being positioned between said valve means and said proximal end of said housing, said sleeve being capable of expanding to move said distal end and said proximal end of said housing further apart, and means for releasably holding said sleeve in a collapsed position.

27. The aspirating device of claim 26 wherein said sleeve is accordion-shaped.

28. The aspirating device of claim 24 wherein said housing side wall includes a collapsible, flexible, bendable, sleeve defining a portion of said passageway, said sleeve being positioned between said valve means and said distal end of said housing, said sleeve being capable of expanding to move said distal end and said proximal end of said housing further apart, and means for releasably holding said sleeve in a collapsed position.

29. The aspirating device of claim 28 wherein said sleeve is accordion-shaped.

30. The aspirating device of claim 1 wherein said housing side wall includes a collapsible, flexible, bendable, sleeve defining a portion of said passageway, said sleeve being capable of expanding to move said distal and said proximal end of said housing further apart, and means for releasably holding said sleeve in a collapsed position.

* * * * *